(12) United States Patent
Ma et al.

(10) Patent No.: US 11,013,794 B2
(45) Date of Patent: May 25, 2021

(54) METHOD FOR PREPARING FOOT-AND-MOUTH DISEASE VACCINES

(71) Applicant: SHANGHAI SHEN LIAN BIOMEDICAL CORPORATION, Shanghai (CN)

(72) Inventors: Guijun Ma, Shanghai (CN); Zhen Zhang, Shanghai (CN); Dongsheng Nie, Shanghai (CN); Panqi Luo, Shanghai (CN)

(*) Notice: Subject to any disclaimer, the term of this patent is extended or adjusted under 35 U.S.C. 154(b) by 131 days.

(21) Appl. No.: 16/467,058

(22) PCT Filed: Dec. 5, 2017

(86) PCT No.: PCT/CN2017/114553
§ 371 (c)(1),
(2) Date: Jun. 6, 2019

(87) PCT Pub. No.: WO2018/103619
PCT Pub. Date: Jun. 14, 2018

(65) Prior Publication Data
US 2019/0275140 A1    Sep. 12, 2019

(30) Foreign Application Priority Data
Dec. 7, 2016  (CN) .......................... 201611113532.1

(51) Int. Cl.
*A61K 39/135*    (2006.01)
*A61P 31/14*    (2006.01)
(Continued)

(52) U.S. Cl.
CPC ............ *A61K 39/135* (2013.01); *A61K 39/12* (2013.01); *A61P 31/14* (2018.01); *B01D 36/00* (2013.01);
(Continued)

(58) Field of Classification Search
None
See application file for complete search history.

(56) References Cited

U.S. PATENT DOCUMENTS

| 2005/0197496 A1* | 9/2005 | Perreault | .................. C07K 1/34 |
| | | | 530/412 |
| 2010/0098725 A1* | 4/2010 | Liu | .......................... A61P 31/16 |
| | | | 424/209.1 |

(Continued)

FOREIGN PATENT DOCUMENTS

| CN | 102631673 A | 8/2012 |
| CN | 103374547 A | 10/2013 |

(Continued)

OTHER PUBLICATIONS

International Search Report of PCT Application No. PCT/CN2017/114553, dated Mar. 8, 2018.

(Continued)

*Primary Examiner* — Shanon A. Foley
(74) *Attorney, Agent, or Firm* — Jun He Law Offices P.C.; Zhaohui Wang

(57) ABSTRACT

The present application relates to a method for preparing a foot-and-mouth disease (FMD) vaccine, comprising the following steps: (i) obtaining cell culture media containing FMD virus; (ii) separating and purifying the cell culture media containing FMD virus by an integrated filtration system with two membranes in combination; and (iii) collecting the concentrated solution containing FMD virus obtained in step (ii). The present application also relates to an FMD vaccine prepared by the method described herein and use thereof in the manufacture of a medicament for preventing animal FMD. The present application further relates to an apparatus for preparing an FMD vaccine, which comprises an integrated filtration system with two membranes in combination.

15 Claims, 5 Drawing Sheets

(51) Int. Cl.
    *A61K 39/12*         (2006.01)
    *B01D 36/00*        (2006.01)
    *A61K 39/00*        (2006.01)

(52) U.S. Cl.
    CPC ............. *A61K 2039/5252* (2013.01); *A61K 2039/552* (2013.01); *C12N 2770/32134* (2013.01)

(56) References Cited

U.S. PATENT DOCUMENTS

2016/0222429 A1*   8/2016   De Villiers .......... C07K 16/065
2019/0275140 A1*   9/2019   Ma ......................... A61P 31/14

FOREIGN PATENT DOCUMENTS

| | | | |
|---|---|---|---|
| CN | 103937754 A | | 7/2014 |
| CN | 106474466 A | | 3/2017 |
| EP | 3015542 A1 | | 5/2016 |
| WO | 2015158353 A1 | | 10/2015 |
| WO | WO 2016115456 | * | 7/2016 |

OTHER PUBLICATIONS

Written Opinion of the International Searching Authority of PCT Application No. PCT/CN2017/114553, dated Mar. 8, 2018.

* cited by examiner

METHOD FOR PREPARING FOOT-AND-MOUTH DISEASE VACCINES

CROSS-REFERENCE TO RELATED APPLICATION

This application is a national stage application under 35 U.S.C. § 371 of PCT International Application No. PCT/CN2017/114553, filed on Dec. 5, 2017, which claims the benefit of Chinese Patent Application No. CN201611113532.1, filed on Dec. 7, 2016, which is hereby incorporated by reference in its entirety.

TECHNICAL FIELD

The present application relates to the field of veterinary biological products, and in particular, to a method for preparing a foot-and-mouth disease (FMD) vaccine, an FMD vaccine prepared by the method, use of the FMD vaccine in the manufacture of a medicament for preventing animal FMD, and an apparatus for preparing an FMD vaccine.

BACKGROUND

FMD is an acute, febrile, highly contagious infectious disease in animals caused by FMD viruses. FMD mainly invades cloven-hoofed animals, and its features for clinical diagnosis include blisters on the skin of oral mucosa, hooves and breast. A variety of FMD vaccines have been developed to control and prevent FMD at present. Regarding the method for preparing FMD vaccines, a simple combination of various separation and purification procedures is currently used in the art. For example, continuous flow centrifugation combined with straight flow filtration, depth filtration, or hollow fiber filtration, PEG precipitation or chromatography, and other means are used to separate and purify the harvested cell culture media containing FMD virus, so as to obtain purified FMD virus vaccines.

However, it is difficult for such a simple combination of the separation and purification procedures to achieve the optimum separation and purification efficiency of each procedure, resulting in an extreme imbalance of product quality, production efficiency, and production cost, which is undesirable.

SUMMARY OF THE INVENTION

The present application relates to a method for preparing an FMD vaccine, an FMD vaccine prepared by the method, use of the FMD vaccine in the manufacture of a medicament for preventing animal FMD, and an apparatus for preparing an FMD vaccine.

In one aspect, the present application provides a method for preparing FMD vaccines, comprising the following steps: (i) obtaining cell culture media containing FMD virus; (ii) separating and purifying the cell culture media containing FMD virus by passing through an integrated filtration system with two membranes in combination, which comprises a microfiltration device and an ultrafiltration device arranged in parallel, wherein the microfiltration device comprises a microfiltration feed tank, a first main pump, and a microfiltration membrane, and the ultrafiltration device comprises a concentrate tank, a second main pump, and an ultrafiltration membrane; wherein the microfiltration device is configured to remove large-particle impurities in the cell culture media containing FMD virus, and the ultrafiltration device is configured to remove small molecular impurities in the cell culture media containing FMD virus; wherein the microfiltration device and the ultrafiltration device run simultaneously to perform microfiltration and ultrafiltration of the cell culture media containing FMD virus at the same time to thereby form a concentrate containing FMD virus in the concentrate tank; and (iii) collecting the concentrate containing FMD virus obtained in step (ii).

In some embodiments, the volume of the concentrate tank is equal to or not more than 1.5 times of the target concentrate volume of the cell culture media containing FMD virus. In some embodiments, the volume of the concentrate tank is ⅕-1/50 of the initial volume of the cell culture media containing FMD virus.

In some embodiments, the microfiltration membrane has a pore size of 0.1-0.45 μm. In some embodiments, the ultrafiltration membrane is a hollow fiber ultrafiltration membrane with a pore size of 100-500 kD.

In some embodiments, after at least a portion of the cell culture media containing FMD virus passing through the microfiltration device, a first diafiltration buffer is further added to the microfiltration feed tank and allowed to pass through the integrated filtration system with two membranes in combination, to obtain a concentrate. In some embodiments, the first diafiltration buffer is a buffer solution with pH of 7.2-9, and conductivity of 5-300 mS/cm. In some embodiments, the volume of the first diafiltration buffer added is 1-5 times of the volume of the microfiltration retentate. In some embodiments, the ultrafiltration filtrate obtained in step (ii) is added as the first diafiltration buffer to the microfiltration feed tank and allowed to pass through the integrated filtration system with two membranes in combination, to obtain a concentrate.

In some embodiments, a second diafiltration buffer is added to the concentrate containing FMD virus obtained in step (ii) to allow small molecular impurities in the concentrate to pass through the ultrafiltration membrane, and thereby to obtain a purified viral concentrate. In some embodiments, the second diafiltration buffer is a buffer solution with pH of 7.2-9, and conductivity of 5-300 mS/cm. In some embodiments, the volume of the second diafiltration buffer added is 1-10 times of the volume of the viral concentrate.

In some embodiments, the microfiltration device is connected to a first constant flow pump, and the ultrafiltration device is connected to a second constant flow pump so as to dynamically control the transmembrane flux. In some embodiments, the first constant flow pump is disposed at the penetration end of the microfiltration device, and the second constant flow pump is disposed at the penetration end of the ultrafiltration device. In some embodiments, the transmembrane flux is 65-100% of the critical membrane flux of the microfiltration membrane or the ultrafiltration membrane. In some embodiments, the transmembrane flux is 10-150 LMH.

In some embodiments, the shear rate through the microfiltration membrane and the ultrafiltration membrane is 1500-4000 s$^{-1}$. In some embodiments, the material per unit membrane area of the microfiltration membrane and the ultrafiltration membrane is 10-500 L/m$^2$.

In some embodiments, the concentrate containing FMD virus is inactivated after step (iii). In some embodiments, the concentrate containing FMD virus is emulsified after inactivation. In some embodiments, the concentrate containing FMD virus is further purified before or after inactivation. In some embodiments, the further purification is performed by PEG precipitation or chromatography. In some embodiments, the chromatography includes exclusion chromatography, ion exchange chromatography, hydrophobic chromatography, and affinity chromatography.

In some embodiments, the microfiltration device and the ultrafiltration device are regenerated by washing after step (iii). In some embodiments, the regeneration by washing comprises the following steps: (a) adding pure water to the microfiltration device and the ultrafiltration device to wash the microfiltration membrane and the ultrafiltration membrane separately, during the washing process, increasing the shear rate through membrane to 8000-16000 $s^{-1}$, and controlling the transmembrane flux at 10-500 LMH; (b) after washing in step (a), adding 0.1-0.5 M NaOH solution to further wash the microfiltration device and the ultrafiltration device, controlling the temperature of solution at 45-55° C., the shear rate through membrane at 8000-16000 $s^{-1}$, the transmembrane flux at 50-500 LMH, and the time at 30-60 mins; and (c) after washing in step (b), flushing the microfiltration device and the ultrafiltration device with pure water separately until the pH value of the microfiltration filtrate and the ultrafiltration filtrate is declined to 9 or less.

In some embodiments, the FMD virus strain includes one or more FMD virus serotypes. In some embodiments, the serotype includes type O, type A, type C, type SAT1, type SAT2, type SAT3, or type Asia1.

In another aspect, the present application relates to an FMD vaccine prepared according to the method described herein.

In another aspect, the present application relates to use of an FMD vaccine prepared according to the method described herein in the manufacture of a medicament for preventing animal FMD.

In another aspect, the present application relates to a method for preventing animal FMD, comprising administering to an animal an immunologically effective amount of an FMD vaccine according to the present application.

In another aspect, the present application relates to an FMD vaccine according to the present application for use in preventing animal FMD.

In another aspect, the present application relates to an apparatus for preparing FMD vaccines, which comprises an integrated filtration system with two membranes in combination, wherein the integrated filtration system with two membranes in combination comprises a microfiltration device and an ultrafiltration device arranged in parallel, wherein the microfiltration device comprises a microfiltration feed tank, a first main pump, and a microfiltration membrane, the ultrafiltration device comprises a concentrate tank, a second main pump, and an ultrafiltration membrane, wherein the microfiltration device is configured to remove large-particle impurities in the cell culture media containing FMD virus, and the ultrafiltration device is configured to remove small molecular impurities in the cell culture media containing FMD virus; wherein the microfiltration device and the ultrafiltration device run simultaneously to perform microfiltration and ultrafiltration of the cell culture media containing FMD virus at the same time to thereby form a concentrate containing FMD virus in the concentrate tank.

In some embodiments, the microfiltration device and the ultrafiltration device are connected to each other, such that both the microfiltration filtrate and the ultrafiltration retentate are retained in the concentrate tank to form a concentrate containing FMD virus.

In some embodiments, the integrated filtration system with two membranes in combination further comprises a first constant flow pump and a second constant flow pump. The microfiltration device is connected to the first constant flow pump, and the ultrafiltration device is connected to the second constant flow pump so as to dynamically control the transmembrane flux. In some embodiments, the first constant flow pump is disposed at the penetration end of the microfiltration device, and the second constant flow pump is disposed at the penetration end of the ultrafiltration device.

BRIEF DESCRIPTION OF THE DRAWINGS

Figure 1:
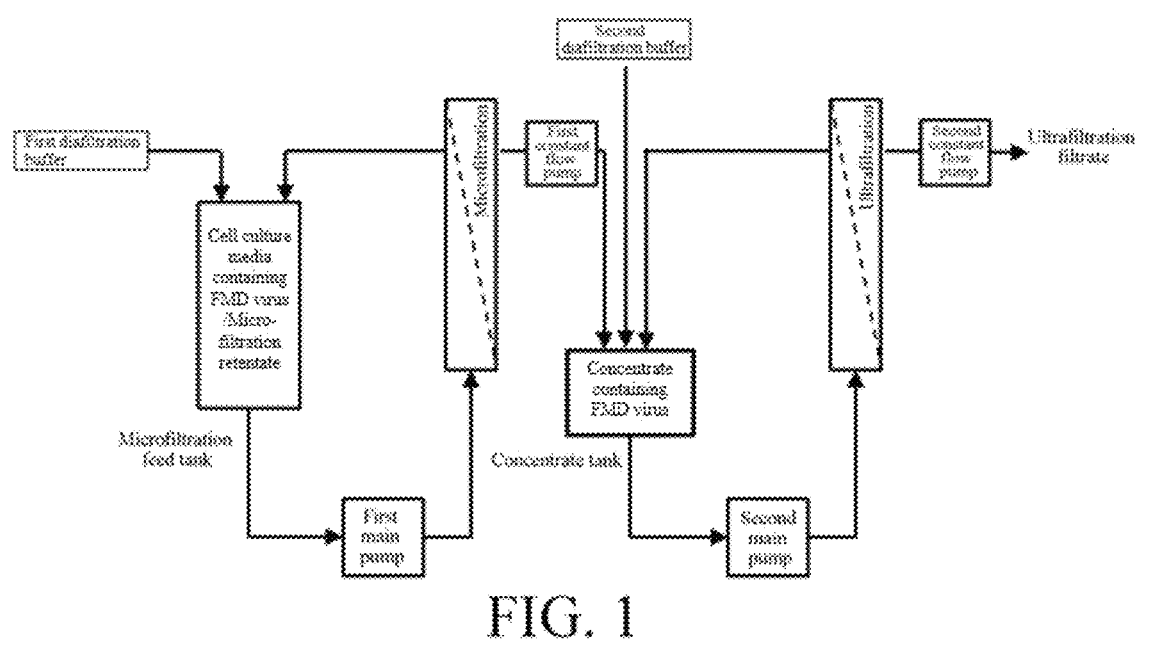

FIG. 1 is a schematic view showing a process for preparing an FMD vaccine provided in Example 1 of the present application.

Figure 2:
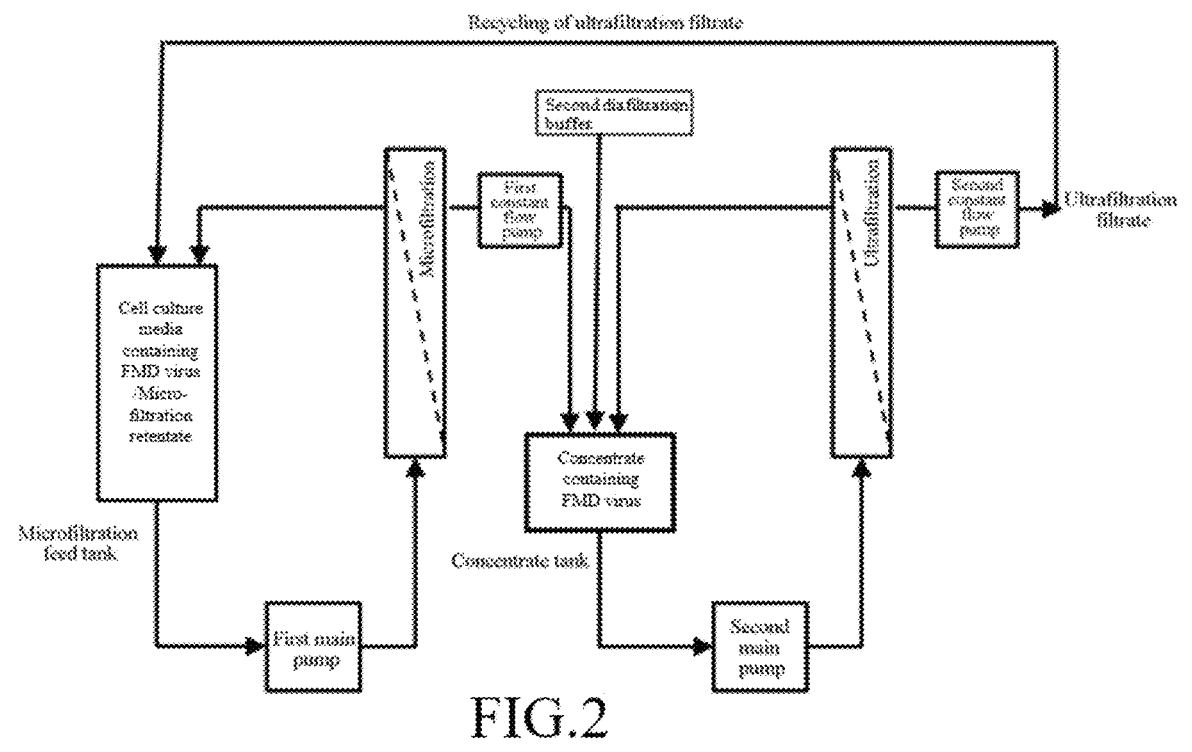

FIG. 2 is a schematic view showing a process for preparing an FMD vaccine provided in Example 2 of the present application.

DETAILED DESCRIPTION OF THE INVENTION

Figure 3:
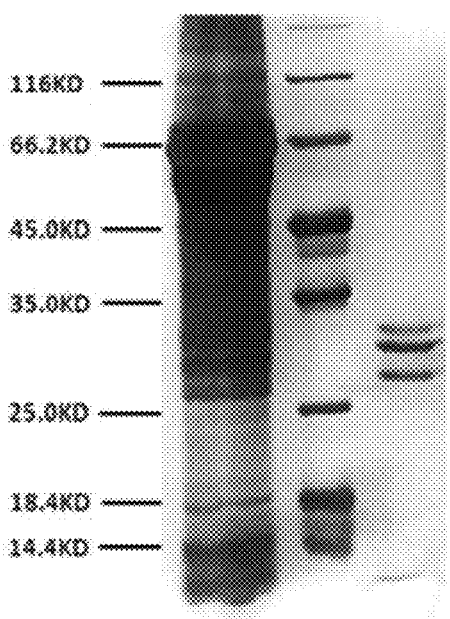
FIG. 3 is an SDS-PAGE pattern of the FMD virus antigen obtained in Example 1 of the present application.

Many aspects and embodiments of the present invention will be disclosed below, however, it will be apparent to those skilled in the art that various equivalent changes and modifications can be made without departing from the spirit and scope of the present application. The various aspects and embodiments disclosed in the present application are intended to be illustrative only and are not intended to limit the scope of the present application as defined by the claims. Unless otherwise indicated, all technical and scientific terms used in this application have the same meaning as commonly understood by one of ordinary skills in the art. All references, patents, and patent applications cited in this application are hereby incorporated by reference in their entirety.

In one aspect, the present application provides a method for preparing FMD vaccines, comprising the following steps: (i) obtaining cell culture media containing FMD virus; (ii) separating and purifying the cell culture media containing FMD virus by passing through an integrated filtration system with two membranes in combination, which comprises a microfiltration device and an ultrafiltration device arranged in parallel, wherein the microfiltration device comprises a microfiltration feed tank, a first main pump, and a microfiltration membrane, and the ultrafiltration device comprises a concentrate tank, a second main pump, and an ultrafiltration membrane; wherein the microfiltration device is configured to remove large-particle impurities in the cell culture media containing FMD virus, and the ultrafiltration device is configured to remove small molecular impurities in the cell culture media containing FMD virus; wherein the microfiltration device and the ultrafiltration device run simultaneously to perform microfiltration and ultrafiltration of the cell culture media containing FMD virus at the same time to thereby form a concentrate containing FMD virus in the concentrate tank; and (iii) collecting the concentrate containing FMD virus obtained in step (ii).

The term "vaccine" as used in the present application refers to a composition comprising one or more antigens having ability to activate the immunity of an organism. After introducing into a host animal, the vaccine can stimulate the host animal to elicit an immune response against one or more antigens.

The term "host animal" as used in the present application refers to an animal that can be infected by FMD virus, and in which the FMD virus can replicate. In some embodiments, the host animal is a cloven-hoofed animal. In some embodiments, the host animal is a domestic animal such as a pig, cow, or sheep. In some embodiments, the host animal is a pig. Infection and replication of FMD virus in host animals may or may not lead to clinical signs of FMD.

The FMD virus described in the present application may include one or more FMD virus serotypes. In some embodiments, the serotype includes type O, type A, type C, type SAT1, type SAT2, type SAT3, or type Asia1. Each main type is subdivided into several subtypes, and more than 70 subtypes have been discovered so far. In some embodiments, the serotype is type A. Without being bound to theory, but it is contemplated that the method for preparing FMD vaccines of the present application is applicable to various FMD virus serotypes or a mixture of these viruses.

The FMD virus described in the present application can be natural FMD virus separated and purified from natural environment, recombinant FMD virus strains obtained by genetic engineering, virus-like particles or recombinant antigens prepared by other expression systems (engineered bacteria, insects, and plants). Recombinant FMD virus or FMD virus peptide fragments can be obtained by a person skilled in the art through well-known genetic engineering methods.

The term "cell culture media containing FMD virus" refers to a cell culture that is infected with FMD virus and allows FMD virus to grow and replicate. Cell culture media containing FMD virus can be prepared using methods well known in the art (refer to, for example, She Daliang et al., Description on Food-and-mouth Disease Vaccine Production Process, *Chinese Journal of Veterinary Medicine*, 2011 45(1): 41-44). Cells suitable for culturing FMD virus include baby hamster kidney cells (BHK21 cells), porcine kidney cells (IBRS-2 cells), bovine kidney cells (MDBK cells), African green monkey kidney cells (Vero cells) and the like. In a preferred embodiment, BHK21 cells are used in the present application to culture FMD virus.

The term "integrated filtration system with two membranes in combination" as used in the present application refers to an integrated filtration system including a microfiltration device and an ultrafiltration device arranged in parallel, connected and cooperated with each other, wherein the microfiltration device comprises a microfiltration feed tank, a first main pump, and a microfiltration membrane; and the ultrafiltration device comprises a concentrate tank, a second main pump, and an ultrafiltration membrane, wherein the microfiltration device and the ultrafiltration device run simultaneously to perform microfiltration and ultrafiltration of cell culture media containing FMD virus at the same time to thereby form a concentrate containing FMD virus in the concentrate tank. In the integrated filtration system with two membranes in combination, the microfiltration device and the ultrafiltration device are arranged in parallel and connected to each other, such that both the microfiltration filtrate and the ultrafiltration retentate reside in the concentrate tank to form a concentrate containing FMD virus.

The term "microfiltration filtrate" as used in the present application refers to a filtrate obtained after the cell culture media containing FMD virus passing through the microfiltration device. The microfiltration device is configured to remove large-particle impurities in the cell culture media containing FMD virus. After passing through the microfiltration device, the amount of large-particle impurities in the microfiltration filtrate is reduced significantly compared with that before passing through the microfiltration device. For example, the microfiltration device can remove at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or even 100% of the large-particle impurities in the cell culture media containing FMD virus, compared with the amount of large-particle impurities in the cell culture media containing FMD virus before passing through the microfiltration device. In some embodiments, the microfiltration device can remove about 30% to about 100%, about 30% to about 90%, about 30% to about 80%, about 40% to about 80%, about 40% to about 90%, about 40% to about 100%, about 50% to about 80%, about 50% to about 90%, about 50% to about 100% (for example, about 60% to about 90%, about 70% to about 90%), about 60% to about 100%, about 70% to about 100%, about 80% to about 100%, about 90% to about 100%, or about 95% to about 100% (for example, about 96% to about 100%, about 97% to about 100%, about 98% to about 100%, about 99% to about 100%, about 95% to about 96%, about 95% to about 97%, about 95% to about 98%, or about 95% to about 99%) of the large-particle impurities in the cell culture media containing FMD virus, compared with the amount of large-particle impurities in the cell culture media containing FMD virus before passing through the microfiltration device.

The term "large-particle impurities" as used in the present application refers to impurities such as cell debris, bacteria, aggregates, and flocs present in the cell culture media containing FMD virus. In certain embodiments, the large-particle impurities have a minimum diameter greater than 0.1 μm. These large-particle impurities have a size larger than the pore size of the microfiltration membrane, and therefore cannot pass through the microfiltration membrane and are retained in the microfiltration feed tank.

When the cell culture media containing FMD virus pass through the microfiltration device, small molecular impurities and FMD virus permeate the microfiltration membrane and are present in the microfiltration filtrate. The microfiltration filtrate further passes through the ultrafiltration device to remove small molecular impurities in the cell culture media containing FMD virus. However, FMD virus cannot pass through the ultrafiltration membrane and are retained in the ultrafiltration retentate.

The term "ultrafiltration retentate" as used in the present application refers to a liquid in the microfiltration filtrate that does not pass through the ultrafiltration membrane, and is thus retained in the concentrate tank of the ultrafiltration device, and is a concentrate containing FMD virus. After passing through the ultrafiltration device, the amount of small molecular impurities in the ultrafiltration retentate is reduced significantly compared with that before passing through the ultrafiltration device. For example, the ultrafiltration device can remove at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or even 100% of the small molecular impurities in the microfiltration filtrate, compared with the amount of small molecular impurities in the microfiltration filtrate before passing through the ultrafiltration device. In some embodiments, the ultrafiltration device can remove about 30% to about 100%, about 30% to about 90%, about 30% to about 80%, about 40% to about 80%, about 40% to about 90%, about 40% to about 100%, about 50% to about 80%, about 50% to about 90%, about 50% to about 100% (for example, about 60% to about 90%, about 70% to about 90%), about 60% to about 100%, about 70% to about 100%, about 80% to about 100%, about 90% to about 100%, or about 95% to about 100% (for example, about 96% to about 100%, about 97% to about 100%, about 98% to about 100%, about 99% to about 100%, about 95% to about 96%, about 95% to about 97%, about 95% to about 98%, or about 95% to about 99%) of the small molecular impurities in the microfiltration filtrate, compared with the amount of small molecular impurities in the microfiltration filtrate before passing through the ultrafiltration device.

The term "small molecular impurities" as used in the present application refers to impurities such as nucleic acids and nucleic acid fragments, host proteins, viral non-structural proteins, protein and viral degradation products, and medium components in the cell culture media containing FMD virus. In some embodiments, small molecular impurities have a size fewer than 500,000 Daltons. These small molecular impurities are smaller in size than the pore size of the ultrafiltration membrane, and therefore can permeate the ultrafiltration membrane, and finally present in the ultrafiltration filtrate. The term "ultrafiltration filtrate" as used in the present application refers to a filtrate obtained after the microfiltration filtrate passing through the ultrafiltration device.

The microfiltration feed tank described in the present application is used for holding the cell culture media containing FMD virus to be separated and purified. Microfiltration retentate not passing through the microfiltration membrane returned to the microfiltration feed tank. The term "microfiltration retentate" as used in the present application refers to a liquid that does not pass through the microfiltration membrane, and is thus retained in the microfiltration feed tank. In some embodiments, the microfiltration retentate and the cell culture media containing FMD virus to be separated and purified are mixed and held in the microfiltration feed tank. In some embodiments, the microfiltration device of the present application has an agitating device to mix the microfiltration retentate and the cell culture media containing FMD virus to be separated and purified in the microfiltration feed tank uniformly.

The concentrate tank of the present application is used to hold the microfiltration filtrate, and also the ultrafiltration retentate that did not pass through the ultrafiltration membrane. In some embodiments, the microfiltration filtrate and the ultrafiltration retentate reside together in the concentrate tank. In some embodiments, the ultrafiltration device of the present application has an agitating device to mix the microfiltration filtrate and the ultrafiltration retentate in the concentrate tank uniformly.

The first main pump of the present application is used to pump the liquid in the microfiltration feed tank continuously into the microfiltration device, and the second main pump of the present application is used to pump the liquid in the concentrate tank continuously into the ultrafiltration device. The microfiltration device and the ultrafiltration device run simultaneously to perform microfiltration and ultrafiltration of the cell culture media containing FMD virus at the same time. In the integrated filtration system with two membranes in combination, microfiltration and ultrafiltration take place in parallel, that is to say, at the same time point, a part of the cell culture media is passing through the microfiltration membrane when another part of the cell culture media is passing through the ultrafiltration membrane. This preparation process is different from a conventional one, where the microfiltration filtrate is collected after all of the cell culture media containing FMD virus has passed through the microfiltration device, and then subjected to ultrafiltration. The integrated filtration system with two membranes in combination according to the present application can not only reduce pipeline connections and site area, but also save filtration time significantly.

In some embodiments, the temperature for microfiltration and ultrafiltration process is 2 to 20° C., such as 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C. or any value within a range defined by any of the two values as provided above. In a preferred embodiment, the temperature for microfiltration and ultrafiltration process is 2 to 8° C. The maintenance of a constant low temperature helps to maintain the structure integrity of FMD virus antigens.

In some embodiments, the volume of the concentrate tank is equal to or not more than 1.5 times of the target concentrate volume. For example, the volume of the concentrate tank is 1 time, 1.1 times, 1.2 times, 1.3 times, 1.4 times, 1.5 times or any value within a range defined by any of the two values as provided above, of the target concentrate volume.

In some embodiments, the volume of the concentrate tank is 1/5-1/50 of the initial volume of the cell culture media containing FMD virus. For example, the volume of the concentrate tank is 1/5, 1/10, 1/15, 1/20, 1/25, 1/30, 1/35, 1/40, 1/45, 1/50, 1/45, 1/50, or any value within a range defined by any of the two values as provided above, of the initial volume of the cell culture media containing FMD virus.

The microfiltration membrane of the present application may be a commercially available microfiltration membrane, such as microfiltration hollow fiber membrane series produced by GE Healthcare Life Sciences, Spectrum Laboratories, Inc., and Asahi Kasei Corporation. In some embodiments, the microfiltration membrane has a pore size of 0.1 μm to 0.45 μm, such as 0.1 μm, 0.15 μm, 0.2 μm, 0.22 μm, 0.25 μm, 0.3 μm, 0.35 μm, 0.4 μm, 0.45 μm or any value within a range defined by any of the two values as provided above. According to the size of FMD virus, the pore size of the microfiltration membrane may be as small as possible, so as to facilitate the recovery of FMD virus antigens and removal of large-particle impurities.

The ultrafiltration membrane of the present application may be a commercially available ultrafiltration membrane, such as ultrafiltration hollow fiber membrane series produced by GE Healthcare Life Sciences, Spectrum Laboratories, Inc., and Asahi Kasei Corporation. In some embodiments, the ultrafiltration membrane is a hollow fiber ultrafiltration membrane with a pore size of 100-500 kD, for example, a hollow fiber ultrafiltration membrane with a pore size of 100 kD, 150 kD, 200 kD, 250 kD, 300 kD, 350 kD, 400 kD, 450 kD, 500 kD, or any value within a range defined by any of the two values as provided above. According to the size of FMD virus, the pore size of the ultrafiltration membrane may be as large as possible, so as to facilitate the recovery of FMD virus antigens and removal of small molecular impurities.

In some embodiments, after at least a portion of the cell culture media containing FMD virus passing through the microfiltration device, a first diafiltration buffer is further added to the microfiltration feed tank and allowed to pass through the integrated filtration system with two membranes in combination, to obtain a concentrate. The term "at least a portion" means at least 30%, at least 40%, at least 50%, at least 55%, at least 60%, at least 65%, at least 70%, at least 75%, at least 80%, at least 85%, at least 90%, at least 95%, at least 96%, at least 97%, at least 98%, at least 99%, or even 100%, or any value within a range defined by any of the two values as provided above. Adding the first diafiltration buffer facilitates FMD virus antigens remaining in the microfiltration feed tank passing through the microfiltration membrane, and going into the ultrafiltration device for enrichment. Washing by the first diafiltration buffer can increase the recovery rate of FMD virus antigens during the microfiltration process.

In some embodiments, the first diafiltration buffer is a buffer solution with pH of 7.2-9 and conductivity of 5-300 mS/cm. In some embodiments, the buffer solution is phosphate buffered saline (PBS), borate buffer, citrate buffer, acetate buffer, barbiturate buffer or trihydroxymethylaminomethane buffer (Tris). In a preferred embodiment, the buffer solution is PBS. In some embodiments, the pH of the buffer solution is 7.2, 7.5, 8.0, 8.5, 9.0, or any value within a range defined by any of the two values as provided above. In some embodiments, the conductivity of the buffer solution is 5 mS/cm, 50 mS/cm, 100 mS/cm, 150 mS/cm, 200 mS/cm, 250 mS/cm, 300 mS/cm or any value within a range defined by any of the two values as provided above.

In some embodiments, the volume of the first diafiltration buffer added is 1-5 times, for example, 1 time, 2 times, 3 times, 4 times, 5 times or any value within a range defined by any of the two values as provided above, of the volume of the microfiltration retentate. In some embodiments, the volume of the first diafiltration buffer used may be ⅕ time, ½ time, 1 time or 2 times of the initial volume of the cell culture media.

In some embodiments, the ultrafiltration filtrate obtained after the microfiltration and ultrafiltration processes is added as the first diafiltration buffer to the microfiltration feed tank, and the FMD virus antigens retained by the microfiltration membrane are washed off into the ultrafiltration device to obtain a concentrate. Thus, it can not only properly recycle resource, greatly reduce the volume of diafiltration buffer, further reduce cost, but also increase the recovery rate of FMD virus antigens.

In some embodiments, a second diafiltration buffer is added to the concentrate containing FMD virus obtained after the microfiltration and ultrafiltration processes, to further allow small molecular impurities retained in the concentrate to pass through the ultrafiltration membrane, and thereby to obtain a concentrate containing purified viruses. The purpose of adding the second diafiltration buffer is to remove small molecular impurities in the ultrafiltration device, decrease the amount of small molecular impurities retained in the ultrafiltration retentate, and thereby improving the purity of FMD virus in the concentrate.

In some embodiments, the second diafiltration buffer is a buffer solution with pH of 7.2-9 and conductivity of 5-300 mS/cm. In some embodiments, the buffer solution is phosphate buffered saline (PBS), borate buffer, citrate buffer, acetate buffer, barbiturate buffer solution or trihydroxymethylaminomethane buffer (Tris). In a preferred embodiment, the buffer solution is phosphate buffered saline. In some embodiments, the pH of the buffer solution is 7.2, 7.5, 8.0, 8.5, 9.0, or any value within a range defined by any of the two values as provided above. In some embodiments, the conductivity of the buffer solution is 5 mS/cm, 50 mS/cm, 100 mS/cm, 150 mS/cm, 200 mS/cm, 250 mS/cm, 300 mS/cm or any value within a range defined by any of the two values as provided above.

In some embodiments, the volume of the second diafiltration buffer added is 1-10 times, for example, 1 time, 2 times, 3 times, 4 times, 5 times, 6 times, 7 times, 8 times, 9 times, 10 times or any value within a range defined by any of the two values as provided above, of the volume of the FMD virus concentrate. The term "FMD virus concentrate" or "concentrate containing FMD virus" used in the present application refers to a solution with reduced amount of large-particle impurities and small molecular impurities after the microfiltration and ultrafiltration processes, which does not pass through the ultrafiltration membrane, and thus is retained in the concentrate tank.

In some embodiments, the microfiltration device is connected to a first constant flow pump, and the ultrafiltration device is connected to a second constant flow pump so as to dynamically control the transmembrane flux. The term "dynamically control" used in the present application refers to maintaining the surface contamination of the microfiltration membrane and ultrafiltration membrane at or below the irreversible contamination threshold by dynamically adjusting the transmembrane flux. For example, as the concentration multiple increases, the constant flow pump needs to be properly adjusted to reduce the transmembrane flux to maintain the surface contamination of the membrane in a state of reversible contamination, so as to delay the decrease in membrane efficiency, and prolong membrane's service life. The term "transmembrane flux" as used in the present application refers to the volume of fluid passing through a unit membrane area in a unit time. In the present application, the unit of transmembrane flux is represented as LMH ($L/m^2*h$), i.e. the volume of fluid passed through per square meter membrane per hour.

The first constant flow pump of the present application is configured to control the transmembrane flux of the microfiltration device, and the second constant flow pump is configured to control the transmembrane flux of the ultrafiltration device. In some embodiments, the first constant flow pump is disposed at the penetration end of the microfiltration device, and the second constant flow pump is disposed at the penetration end of the ultrafiltration device so as to achieve the dynamic control of the transmembrane flux.

The transmembrane flux can be controlled by changing the concentration multiple (namely, the multiple is calculated by dividing the volume of concentrated cell culture media by its initial volume) of the cell culture media containing FMD virus. Preferably, when the concentration multiple is ⅕-1/50, the transmembrane flux can be maintained within a reasonable range. Otherwise, a too high concentration multiple may lead to a too low transmembrane flux, and too long operation time; while a too low concentration multiple may lead to low recovery of the FMD virus antigen, and thus a large volume of diafiltration buffer is required.

In some embodiments, the transmembrane flux is below the critical transmembrane flux of the microfiltration membrane or the ultrafiltration membrane. The term "critical transmembrane flux" used in the present application is a critical value between reversible contamination and irreversible contamination of a microfiltration membrane or an ultrafiltration membrane. When the transmembrane flux is lower than the critical transmembrane flux, the microfiltration membrane or ultrafiltration membrane is in a reversible state of contamination. When the transmembrane flux is higher than the critical transmembrane flux, the microfiltration membrane or ultrafiltration membrane is in an irreversible state of contamination. The critical transmembrane flux varies with the pore size, material, structure of the membrane, and can be affected by the sample state and operating conditions. The critical transmembrane flux can be determined by a variety of methods known in the art, for example by detecting film pressure after increasing transmembrane flux gradually, or by detecting transmembrane flux after increasing film pressure gradually (see, for example, R. W. Field et al., Critical flux concept for microfiltration fouling, *Journal of Membrane Science*, 1995, 100(3): 259-272).

In the process of separation and purification, the transmembrane flux is an important factor that affects the recovery rate of FMD virus and the service life of membrane. If the transmembrane flux is higher than the critical transmembrane flux, it may cause irreversible contamination of membrane, thus reducing the service life of membrane. To the contrary, if the transmembrane flux is lower than the critical transmembrane flux, it may lead to an increasingly prolonged production time and an elevated cost of maintaining the stability of production system, thus resulting in low production efficiency. Therefore, it is necessary to choose a suitable transmembrane flux, which is below the critical transmembrane flux, to ensure a high recovery rate of FMD virus, the removal of impurities, high stability of the system, and also a long service time of membrane, thereby greatly reducing the production cost. In some embodiments, the transmembrane flux is 65% to 100% of the critical transmembrane flux of the microfiltration membrane or the ultrafiltration membrane. For example, the transmembrane flux is 65%, 70%, 75%, 80%, 85%, 90%, 91%, 92%, 93%, 94%, 95%, 96%, 97%, 98%, 99%, 100%, or any value within a range defined by any of the two values as provided above, of the critical transmembrane flux of the microfiltration membrane or the ultrafiltration membrane. In some embodiments, the transmembrane flux is 10-150 LMH, for example, 10 LMH, 20 LMH, 30 LMH, 40 LMH, 50 LMH, 60 LMH, 70 LMH, 80 LMH, 90 LMH, 100 LMH, 110 LMH, 120 LMH, 130 LMH, 140 LMH, 150 LMH or any value within a range defined by any of the two values as provided above.

The shear rate at which the fluid passes through the microfiltration membrane and the ultrafiltration membrane is also an important factor affecting the recovery rate of FMD virus and the membrane's service life. Adopting a higher shear rate than the tolerated value of FMD virus antigen will cause damage and dissociation of virus, thus reducing the yield. While a very low shear rate reduces the transmembrane flux, and thus decreases the separation efficacy of membrane. In some embodiments, the shear rate through the microfiltration membrane and the ultrafiltration membrane is 1500-4000 $s^{-1}$. The loss of FMD virus antigen is not more than 5% at this rate. For example, the shear rate through the microfiltration membrane and the ultrafiltration membrane is 1500 $s^{-1}$, 1600 $s^{-1}$, 1700 $s^{-1}$, 1800 $s^{-1}$, 1900 $s^{-1}$, 2000 $s^{-1}$, 2100 $s^{-1}$, 2200 $s^{-1}$, 2300 $s^{-1}$, 2400 $s^{-1}$, 2500 $s^{-1}$, 2600 $s^{-1}$, 2700 $s^{-1}$, 2800 $s^{-1}$, 2900 $s^{-1}$, 3000 $s^{-1}$, 3100 $s^{-1}$, 3200 $s^{-1}$, 3300 $s^{-1}$, 3400 $s^{-1}$, 3500 $s^{-1}$, 3600 $s^{-1}$, 3700 $s^{-1}$, 3800 $s^{-1}$, 3900 $s^{-1}$, 4000 $s^{-1}$, or any value within a range defined by any of the two values as provided above.

Material per unit membrane area of the microfiltration membrane and the ultrafiltration membrane is also an important factor that affects the recovery rate and the membrane's service life. Material per unit membrane area is calculated by dividing the volume of the liquid to be processed by the membrane area. If the value of material per unit membrane area is higher than membrane load, it will be difficult to maintain the operation conditions below the critical transmembrane flux, resulting in an irreversible contamination of the membrane, or a prolonged operation time and low production efficiency. To the contrary, if the value of material per unit membrane area is too low, the efficiency of the membrane is not fully exerted, thus increasing the production cost. Therefore, it is necessary to select a suitable value of material per unit membrane area, so as to extend the membrane's service life as long as possible, while ensuring a high yield. In some embodiments, the material per unit membrane of the microfiltration membrane and the ultrafiltration membrane is 10-500 $L/m^2$, for example, 10 $L/m^2$, 50 $L/m^2$, 100 $L/m^2$, 150 $L/m^2$, 200 $L/m^2$, 250 $L/m^2$, 300 $L/m^2$, 350 $L/m^2$, 400 $L/m^2$, 450 $L/m^2$, 500 $L/m^2$, or any value within a range defined by any of the two values as provided above.

In some embodiments, the concentrate containing FMD virus is inactivated after step (iii). The concentrate containing FMD virus can be inactivated by a method commonly used in the art. For example, the concentrated and purified concentrate containing FMD virus is inactivated with 1 mM to 3 mM diethyleneimine (BEI) at 30° C. for 28 hours, then blocked for 20 min by adding 1.6% (v/v) of a blocking agent sodium thiosulfate, and stored at 4° C. for later use; or the concentrated and purified concentrate containing the FMD virus is inactivated at 37° C. for 3-4 days by adding β-propiolactone at a ratio of 1/4000, and then stored at 4° C. for later use (see, for example, She Daliang et al., Description on Food-and-mouth Disease Vaccine Production Process, *Chinese Journal of Veterinary Medicine*, 2011 45(1): 41-44).

In some embodiments, the concentrate containing FMD virus is emulsified after inactivation. The concentrate containing FMD virus can be emulsified by a method commonly used in the art. For example, an aqueous phase is prepared first, that is, the concentrate containing FMD virus is diluted with a sterilized physiological saline; then an oil phase is prepared, that is, an oil phase adjuvant, such as Montanide ISA206 is autoclaved at 120° C.; the aqueous phase and the oil phase are preheated to 30° C. before use. To prepare a water-in-oil-in-water (W/O/W) emulsion vaccine, the preheated aqueous phase is added slowly to the preheated oil phase at the weight ratio of 1:1, while stirring at a low speed, and then emulsify for about 20 min to allow the phases fully mixed. The emulsion vaccine is stored at 4° C.

In some embodiments, the concentrate containing FMD virus is further purified before or after the inactivation. In some embodiments, the further purification is achieved through PEG (polyethylene glycol) precipitation or chromatography.

PEG precipitation is a method that separates FMD virus from the other impurities through adding PEG to the concentrate to change its physical and chemical parameters and to control the solubility of various components therein. The commonly used precipitant includes PEG2000, PEG4000, PEG6000 and the like. The general operation steps include: adding PEG to the concentrate containing FMD virus to form a precipitate; allowing the concentrate containing precipitate to store for a period of time to promote the formation of precipitated particles, and then collecting the precipitate by centrifugation or filtration.

In some embodiments, the chromatography includes size exclusion chromatography, ion exchange chromatography, hydrophobic chromatography, and affinity chromatography.

Size exclusion chromatography is also known as gel chromatography, which separates FMD virus from the other impurities based on their differences in molecular weights and infiltration levels in chromatography media. Gel chromatography media include polyacrylamide gels, crosslinked dextran gels, agarose gels, polyphenylene gels, silica gels, polymethacrylates, and the like. Various gel chromatography media are also commercially available, such as media produced by GE Healthcare Life Sciences, Tosho, Merck Millipore, Bestchrom Biotechnology Co., LTD, NanoMicro, Co, Ltd, Xi'an Sunresin New Materials Co., Ltd, and so on. In some embodiments, the gel chromatography media used is a cross-linked dextran gel. Further purification of the concentrate containing FMD virus by gel chromatography is generally achieved by adding gel chromatography media to the concentrate containing FMD virus, then packing the media into a chromatographic column, and conducting chromatography; or adding the concentrate containing FMD virus directly to a chromatographic column filled with the gel chromatography media and conducting chromatography.

Ion exchange chromatography separates FMD virus from the other impurities through the interaction of charged residues on ion exchange media with different charged components in the concentrate containing FMD virus, thereby further purifying FMD virus. Ion exchange chromatography can be divided into Cation-Exchange chromatography and Anion-Exchange chromatography, depending on different charges (positive or negative) on the surface of ion exchange chromatography media. In some embodiments, the used ion exchange residues on the surface of media include diethylaminoethyl (DEAE), quaternary amino (Q), diethylaminopropyl (ANX), carboxymethyl (CM), and sulfonic acid group (SP) and so on. Various ion exchange chromatography media are also commercially available, such as the media produced by GE Healthcare Life Sciences, Tosho, Merck Millipore, Bestchrom Biotechnology Co., LTD, NanoMicro, Co, Ltd, Xi'an Sunresin New Materials Co., Ltd, and so on. Further purification of the concentrate containing FMD virus by ion exchange chromatography is generally carried out by adding ion exchange chromatography media to the concentrate containing FMD virus, then packing the media into a chromatographic column, and conducting chromatography; or adding the concentrate containing FMD virus directly to a chromatographic column filled with ion exchange chromatography media and conducting chromatography.

Hydrophobic chromatography separates FMD virus, which can adsorb to the media, from impurities in the concentrate containing FMD, which do not or weakly adsorb to the media, through the interaction between the hydrophobic group on hydrophobic chromatography media and that on the surface of FMD virus. In some embodiments, the hydrophobic group on the surface of used hydrophobic chromatography media is butyl, butylthio, phenyl, or octyl. Various hydrophobic chromatography media are also commercially available, such as the media produced by GE Healthcare Life Sciences, Tosho, Merck Millipore, Bestchrom Biotechnology Co., LTD, NanoMicro, Co, Ltd, Xi'an Sunresin New Materials Co., Ltd, and so on. Further purification of the concentrate containing FMD virus by hydrophobic chromatography is generally carried out by adding hydrophobic chromatography media to the concentrate containing FMD virus, then packing the media into a chromatographic column, and conducting chromatography; or adding the concentrate containing FMD virus directly to a chromatographic column filled with hydrophobic chromatography media and conducting chromatography.

In the affinity chromatography, an affinity-molecule media with a special molecular structure is made into a solid phase adsorbent and filled in a chromatographic column. The column separates FMD virus from impurities by adsorbing virus, which exhibits affinity with media. Impurities not showing affinity with media are directly expelled. Then the bound FMD virus is eluted off by using an appropriate eluent or by changing the binding condition. In some embodiments, the adsorbents used are alumina, silica gel, polyamide, and the like. Various affinity-molecule media are also commercially available, such as heparin affinity matrix. Further purification of the concentrate containing FMD virus by affinity chromatography is generally carried out by adding the affinity-molecule media to the concentrate containing FMD virus, then packing the media into a chromatographic column, and conducting chromatography; or adding the concentrate containing FMD virus directly to a chromatographic column filled with affinity chromatography media and conducting chromatography.

In some embodiments, the microfiltration device and the ultrafiltration device are regenerated by washing after step (iii). The water flux of the microfiltration membrane in the microfiltration device and the ultrafiltration membrane in the ultrafiltration device may be reduced with the increase of running time during long-term operation, that is, membrane fouling occurs. Therefore, it is necessary to wash and regenerate the microfiltration membrane and the ultrafiltration membrane, recover the membrane performance, prolong the membrane's service life, thereby reducing the cost of production.

In some embodiments, wash and regeneration process comprises the following steps: (a) adding pure water to the microfiltration device and the ultrafiltration device to wash the microfiltration membrane and the ultrafiltration membrane separately, during the washing process, increasing the shear rate through membrane to 8000-16000 $s^{-1}$, and controlling the transmembrane flux at 10-500 LMH; (b) after washing step in step (a), adding 0.1-0.5 M NaOH solution to further wash the microfiltration device and the ultrafiltration device, controlling the temperature of solution at 45-55° C., the shear rate through membrane at 8000-16000 $s^{-1}$, the transmembrane flux at 50-500 LMH, and the time at 30-60 min; and (c) after washing step in step (b), flushing the microfiltration device and the ultrafiltration device separately with pure water until the pH value of the microfiltration filtrate and the ultrafiltration filtrate is declined to 9 or less.

In some embodiments, the shear rate in step (a) is increased to 8000 $s^{-1}$, 9000 $s^{-1}$, 10000 $s^{-1}$, 11000 $s^{-1}$, 12000 $s^{-1}$, 13000 $s^{-1}$, 14000 $s^{-1}$, 15000 $s^{-1}$, 16000 $s^{-1}$, or any value within a range defined by any of the two values as provided above, and control the transmembrane flux at 10 LMH, 50 LMH, 100 LMH, 150 LMH, 200 LMH, 250 LMH, 300 LMH, 350 LMH, 400 LMH, 450 LMH, 500 LMH or any value within a range defined by any of the two values as provided above.

In some embodiments, the temperature of NaOH solution in step (b) is 45° C., 46° C., 47° C., 48° C., 49° C., 50° C., 51° C., 52° C., 53° C., 54° C., 55° C. or any value within a range defined by any of the two values as provided above. The shear rate through membrane is 8000 $s^{-1}$, 9000 $s^{-1}$, 10000 $s^{-1}$, 11000 $s^{-1}$, 12000 $s^{-1}$, 13000 $s^{-1}$, 14000 $s^{-1}$, 15000 $s^{-1}$, 16000 $s^{-1}$ or any value within a range defined by any of the two values as provided above. The transmembrane flux is controlled at 50 LMH, 100 LMH, 150 LMH, 200 LMH, 250 LMH, 300 LMH, 350 LMH, 400 LMH, 450 LMH, 500 LMH or any value within a range defined by any of the two values as provided above. The time is 30 min, 35 min, 40 min, 45 min, 50 min, 55 min, 60 min, or any value within a range defined by any of the two values as provided above.

In some embodiments, the pH value in step (c) is declined to 9, 8.5, 8.0, 7.5, 7.0 or any value within a range defined by any of the two values as provided above.

In some embodiments, during wash and regeneration step, the transmembrane flux is still dynamically controlled to prevent some cleaning problems caused by deep penetration of contaminants into the membrane pores under high transmembrane pressure. Moreover, a warm strong alkali solution can hydrolyze contaminants, so that the membrane performance can be well maintained.

In another aspect, the present application relates to an FMD vaccine prepared according to the method described herein. In some embodiments, the FMD vaccine of the present application can be administered to an animal via an appropriate route including, but not limited to, an oral route, an injection route (such as intravenous injection, intramuscular injection, subcutaneous injection, intradermal injection, intracardiac injection, intrathecal injection, intrapleural injection, and intraperitoneal injection, etc.), a mucosal route (such as intranasal administration, and intraoral administration, etc.), a sublingual route, a rectal route, a transdermal route, an intraocular route, and a pulmonary route. In some embodiments, the FMD vaccine of the present application can be administered by injection. As is known to those skilled in the art, the amount of FMD vaccine used varies depending on the activity of the active ingredient, the age and body weight of the individual to be administered, and other factors. One skilled in the art can readily determine the most appropriate dosage of the vaccine based on the factors affecting dosage mentioned above.

The immunological potency of the FMD vaccine prepared according to the methods described herein can be tested by a variety of known methods. Many assays for assessing the immunological efficacy of vaccines are provided in the prior art, such as virus challenge assays, serological assays, and the like. The virus challenge assay is conducted by artificially infecting the inoculated animals with a strong virus, and the immunological efficacy of the vaccine is determined by the incidence of animal infections. Virus challenge assay is the most effective method to directly reflect the immunological efficacy of the vaccine. Therefore, this assay is required to evaluate the immunological efficacy of veterinary vaccines by many countries including China. The detailed procedure of virus challenge assay may be found in sections concerning the determination of the median protective dose ($PD_{50}$), which is described in the Chinese Veterinary Pharmacopoeia, 2010 Edition. The immunological efficacy of a vaccine can also be evaluated by serological tests, such as determining the level of antibody in the serum of immunized animals by ELISA (i.e., enzyme-linked immunosorbent assay). An ELISA test usually includes the following procedures: firstly, adsorb antigens (or antibodies) to a solid phase carrier, and then add in antibody (or antigen)-enzyme conjugates (labels). After the conjugates binding to the antigen (or antibody), which is adsorbed on the solid phase carrier, add in a substrate specific to the enzyme. The enzyme can hydrolyze or oxidize/deoxidize the specified substrate into a uniform colored end product. The intensity of color is proportional to the amount of antigen (or antibody) to be tested. There is a correlation between these serological indicators and the potency of vaccines, which can be used to primarily evaluate the immunological potency of the vaccine. People skilled in the art can choose a suitable test based on some practical factors, such as experimental conditions and objectives.

In another aspect, the present application relates to use of an FMD vaccine prepared according to the method described herein in the manufacture of a medicament for preventing animal FMD. In some embodiments, the animal FMD is FMD in swine, cow, or sheep. In some embodiments, the animal FMD is FMD in swine. In some embodiments, the animal FMD disease is FMD serotype A in swine.

In another aspect, the present application relates to a method for preventing animal FMD, comprising administering to an animal an immunologically effective amount of an FMD vaccine according to the present application. The term "immunologically effective amount" as used herein, refers to an amount that elicits an immune response against FMD virus in a vaccinated animal. The immunologically effective amount varies according to the animal species, strain, age, weight, and health status. In some embodiments, the animal FMD is FMD in swine, cow, or sheep. In some embodiments, the animal FMD is FMD in swine. In some embodiments, the animal FMD is FMD serotype A in swine.

In another aspect, the present application relates to an FMD vaccine according to the present application for use in preventing animal FMD. In some embodiments, the animal FMD is FMD in swine, cow, or sheep. In some embodiments, the animal FMD is FMD in swine. In some embodiments, the animal FMD is FMD serotype A in swine.

In another aspect, the present application relates to an apparatus for preparing an FMD vaccine, which comprises an integrated filtration system with two membranes in combination, wherein the integrated filtration system with two membranes in combination comprises a microfiltration device and an ultrafiltration device arranged in parallel, wherein the microfiltration device comprises a microfiltration feed tank, a first main pump, and a microfiltration membrane, the ultrafiltration device comprises a concentrate tank, a second main pump, and an ultrafiltration membrane, wherein the microfiltration device is configured to remove large-particle impurities in the cell culture media containing FMD virus, and the ultrafiltration device is configured to remove small molecular impurities in the cell culture media containing FMD virus, wherein the microfiltration device and the ultrafiltration device run simultaneously to perform microfiltration and ultrafiltration of the cell culture media containing FMD virus at the same time to thereby form a concentrate containing FMD virus in the concentrate tank. In some embodiments, the microfiltration device and the ultrafiltration device are connected to each other, such that both the microfiltration filtrate and the ultrafiltration retentate are retained in the concentrate tank to form a concentrate containing FMD virus.

In some embodiments, the integrated filtration system with two membranes in combination further comprises a first constant flow pump and a second constant flow pump. The microfiltration device is connected to the first constant flow pump, and the ultrafiltration device is connected to the second constant flow pump so as to dynamically control the transmembrane flux. In some embodiments, the first constant flow pump is disposed at the penetration end of the microfiltration device, and the second constant flow pump is disposed at the penetration end of the ultrafiltration device.

EMBODIMENTS

Hereinafter, the present invention is described in detail by way of specific examples. All the biological materials involved in the examples, such as FMD virus strain, culture medium, tool enzyme, and buffer solution, as well as various culture methods, virus inactivation, purification, refining and other processes, are well-known to those skilled in the art, and reference may be made to Sambrook et al. "Molecular Cloning", (A Laboratory Manual, Cold Spring Harbor, 1989) and "Short Protocols in Molecular Biology" (Edited by Ausubel F. et al., translated by Yan Ziying et al., Beijing: Science Press, 1998).

Example 1

This example provides a method for preparing an FMD vaccine, in which the cell culture media containing FMD virus was purified by an integrated filtration system with two membranes in combination. Specifically, the method comprises the following steps:

(1) An integrated filtration system with two membranes in combination was constructed, as shown in FIG. 1. The microfiltration membrane (pore size: 0.2 μm, inner diameter: 1 mm, and membrane area: 110 cm$^2$) and the ultrafiltration membrane (pore size: 500 kD, inner diameter: 1 mm, and membrane area: 110 cm$^2$) were equilibrated with a PBS buffer (pH 7.6). The shear rate, temperature, and transmembrane flux for the microfiltration membrane and the ultrafiltration membrane were controlled at 4000 s$^{-1}$, 2-10° C., and 63 LMH, respectively. The volume of PBS buffer (pH 7.6) in the concentrate tank was maintained at 58 mL.

(2) Cell culture media containing FMD virus A/GDMM/2013 (wherein the antigen concentration was 2.3 μg/mL) obtained after BHK21 cells suspension culture was added into the microfiltration feed tank at a material per unit membrane area of 80 L/m$^2$, and subjected to microfiltration and ultrafiltration through the integrated filtration system with two membranes in combination. When the volume of the cell culture media containing FMD virus was decreased to 1/5 of the initial volume, the transmembrane flux through the microfiltration membrane and ultrafiltration membrane was adjusted to 49.5 LMH. When the volume of the cell culture media containing FMD virus was decreased to 1/10 of the initial volume, the transmembrane flux through the microfiltration membrane and ultrafiltration membrane was adjusted to 40.5 LMH.

(3) When the volume of the cell culture media containing FMD virus was decreased to 1/15 of the initial volume, 118 mL (2 times of the volume of concentrate tank) of PBS buffer (pH of 7.6, conductivity of 31 mS/cm) was added as a first diafiltration buffer to the microfiltration feed tank at a flow rate (74.25 mL/min) equal to that of the ultrafiltration filtrate for microfiltration process.

(4) After completing the microfiltration process, the valve at the penetration end of the microfiltration device and the first constant flow pump were closed. Then, 259 mL (4.4 times of the volume of concentrate tank) of PBS buffer (pH of 7.6, conductivity of 31 mS/cm) was added as a second diafiltration buffer to the concentrate tank at a flow rate (74.25 mL/min) equal to that of the ultrafiltration filtrate for ultrafiltration process.

Figure 4:
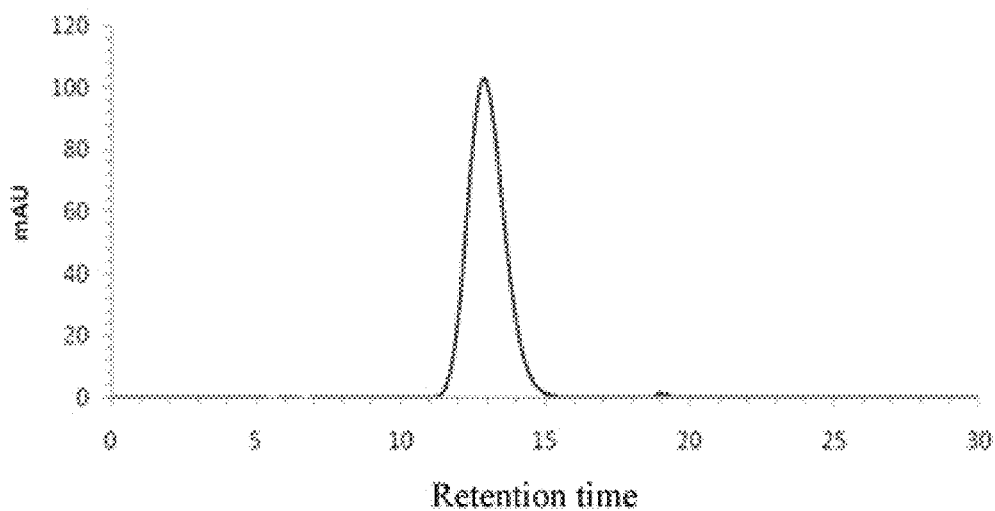
FIG. 4 shows the HPLC detection results of the FMD virus antigen obtained in Example 1 of the present application.

(5) The concentrate containing FMD virus in the concentrate tank was collected. The sodium dodecyl sulfate-polyacrylamide gel electrophoresis (SDS-PAGE) pattern of FMD virus antigen was shown in FIG. 3. The result of high performance liquid chromatography (HPLC) was shown in FIG. 4.

The concentration and total protein content of the FMD virus solution were determined. The concentration of FMD virus antigen was 34.2 μg/mL, the removal rate of impurities was more than 98%, and the total yield of the obtained FMD virus antigen was 98%.

Example 2

This example provides a method for preparing an FMD vaccine, in which the cell culture media containing FMD virus was purified by an integrated filtration system with two membranes in combination, and then purified by chromatography (i.e. refining). Specifically, the method comprises the following steps:

(1) An integrated filtration system with two membranes in combination was constructed, as shown in FIG. 2. The microfiltration membrane (pore size: 0.45 μm, inner diameter: 1 mm, membrane area: 110 cm$^2$) and the ultrafiltration membrane (pore size: 300 kD, inner diameter: 1 mm, membrane area: 110 cm$^2$) were equilibrated with a PBS buffer (pH 7.6). The shear rate, temperature, and transmembrane flux for the microfiltration membrane and the ultrafiltration membrane was controlled at 1500 s$^{-1}$, 2-10° C., and 36 LMH, respectively. The volume of PBS buffer (pH 7.6) in concentrate tank was maintained at 58 mL.

(2) Cell culture media containing FMD virus A/GDMM/2013 (wherein the antigen concentration was 2.3 μg/mL) obtained after BHK21 cells suspension culture was added into the microfiltration feed tank at a material per membrane area of 80 L/m$^2$, and subjected to microfiltration and ultrafiltration through the integrated filtration system with two membranes in combination. When the volume of the cell culture media containing FMD virus was decreased to 1/5 of the initial volume, the transmembrane flux through the microfiltration membrane and ultrafiltration membrane was adjusted to 28.2 LMH. When the volume of the cell culture media containing FMD virus was decreased to 1/10 of the initial volume, the transmembrane flux through the microfiltration membrane and ultrafiltration membrane was adjusted to 23.1 LMH.

(3) When the volume of the cell culture media containing FMD virus was decreased to 1/15 of the initial volume, 118 mL (2 times of the volume of concentrate tank) of ultrafiltration filtrate was refluxed as a first diafiltration buffer to the microfiltration feed tank at a flow rate (42.4 mL/min) equal to that of the ultrafiltration filtrate for microfiltration process.

(4) After completing the microfiltration process, the valve at the penetration end of the microfiltration device and the first constant flow pump were closed. Then, 259 mL (4.4 times of the volume of concentrate tank) of PBS buffer (pH of 7.6, conductivity of 100 mS/cm) was added as a second diafiltration buffer to the concentrate tank at a flow rate (42.4 mL/min) equal to that of the ultrafiltration filtrate for ultrafiltration process.

(5) The concentrate containing FMD virus obtained in Step (4) was loaded to Capto butyl chromatographic media, which have been rinsed with PBS buffer (pH of 7.6, conductivity of 90 ms/cm). After washing with 5 column volumes of PBS buffer (pH of 7.6, conductivity of 90 mS/cm), FMD virus antigen was eluted off the column with PBS buffer (pH of 7.6, conductivity of 5 mS/cm).

The antigen concentration, total protein concentration, and nucleic acid residues of the eluted FMD virus solution were determined. The concentration of FMD virus antigen was 32 μg/mL, the removal rate of host nucleic acids was more than 99%, the removal rate of impurity proteins was more than 99%, and the total yield of the obtained FMD virus antigen was 92%.

Example 3

This example provides a method for preparing an FMD vaccine, in which the cell culture media containing FMD virus was purified by an integrated filtration system with two membranes in combination in large scale. Specifically, the method comprises the following steps:

(1) An integrated filtration system with two membranes in combination was constructed, as shown in FIG. 1. The microfiltration membrane (pore size: 0.2 μm, inner diameter: 1 mm, and membrane area: 38 m$^2$) and the ultrafiltration membrane (pore size: 500 kD, inner diameter: 1 mm, and membrane area: 36 m$^2$) were equilibrated with PBS buffer (pH 7.6). The shear rate and temperature for the microfiltration membrane and the ultrafiltration membrane were controlled at 2000 s$^{-1}$ and 2-10° C., respectively. The transmembrane flux through the microfiltration membrane and ultrafiltration membrane was controlled at 41.8 LMH and 39.6 LMH, respectively (wherein keeping a transmembrane flux difference between two membranes was to maintain the same filtrate flow rate). 200 L of PBS buffer (pH 7.6) was maintained in both the microfiltration feed tank and the concentrate tank.

(2) Cell culture media containing FMD virus A/GDMM/2013 (wherein the antigen concentration was 2.3 μg/mL) obtained after BHK21 cells suspension culture was added into the microfiltration feed tank at a material per unit membrane area of 23.76 L/m$^2$, and subjected to microfiltration and ultrafiltration by the integrated filtration system with two membranes in combination. After 2400 L cell culture media containing FMD virus was pumped into the integrated filtration system with two membranes in combination, the feed rate was adjusted to 19.8 L/min, and the transmembrane flux through microfiltration membrane and ultrafiltration membrane was adjusted to 31.2 LMH, and 33 LMH, respectively. After 300 L cell culture media containing FMD virus was additionally pumped into the integrated filtration system with two membranes in combination, the feed rate was adjusted to 16.2 L/min, and the transmembrane flux through microfiltration membrane and ultrafiltration membrane was adjusted to 25.5 LMH, and 27 LMH, respectively.

(3) After the cell culture media containing FMD virus (3000 L in total) was totally pumped into the integrated filtration system with two membranes in combination, 400 L (2 times of the volume of concentrate tank) of PBS buffer (pH of 7.6, conductivity of 31 mS/cm) was added as a first diafiltration buffer to the microfiltration feed tank at a flow rate (16.2 L/min) equal to that of the ultrafiltration filtrate for microfiltration process.

(4) After completing the microfiltration process, the valve at the penetration end of microfiltration device was closed. Then, 1000 L (5 times of the volume of concentrate tank) of PBS buffer (pH of 7.6, conductivity of 31 mS/cm) was added as the second diafiltration buffer to the concentrate tank at a flow rate (16.2 L/min) equal to that of the ultrafiltration filtrate for ultrafiltration process.

(5) The concentrate containing FMD virus in the concentrate tank was collected.

The FMD virus antigen concentration and total protein concentration were determined. The FMD virus antigen concentration was 30.2 μg/mL, the removal rate of impurity proteins was more than 94%, and the total yield of the obtained FMD virus antigen was 96%.

Example 4

This example prepared inactivated FMD vaccines, in which antigen was either purified or refined, and the immunological efficacy of the prepared vaccines was tested in animals. The specific steps were as follows:

(1) The purified FMD virus antigen prepared in Example 1 and the refined FMD virus pathogen prepared in Example 2 were inactivated with diethyleneimine (BEI), respectively, and then blocked by adding sodium thiosulfate.

(2) To prepare porcine FMD A-type inactivated vaccine, in which antigen was either purified or refined, the inactivated FMD antigen was sterilized by passing through a microfiltration membrane with a pore size of 0.22 μm, and then diluted to 20 μg/mL by adding PBST buffer (pH 7.4) (i.e. adding Tween-20 in PBS buffer) at a volume ratio of 10:7 (antigen solution to buffer solution), then emulsified with 206 adjuvant at a weight ratio of 1:1, and sub-packed.

(3) 12 male specific pathogen-free pigs (SPF pigs) were selected and divided into two groups, 10 in the test group and 2 in the control group. For 5 SPF pigs in the test group, each was injected intramuscularly at the neck with 1 mL of porcine FMD A-type inactivated vaccine, in which antigen was purified. For the rest 5 SPF pigs in the test group, each was injected intramuscularly at the neck with 1 mL of porcine FMD A-type inactivated vaccine, in which antigen was refined. The 2 SPF pigs in the control group were not immunized. 28 days after immunization, each SPF pig was challenged with 0.5 ml of pandemic FMD virus type A containing 10$^5$ TCID50, and the FMD symptoms in pigs were observed for 15 days.

The results showed that no adverse reactions were observed in all the immunized pigs in the test group, and no FMD symptoms were observed, while all the unimmunized pigs in the control group died. Thus it can be seen that the immune protection rate was 100% for both inactivated purified and refined porcine FMD A-type vaccines. Moreover, this example also showed that FMD virus antigen prepared by the present integrated filtration system with two membranes in combination has achieved sufficient purity, which was immunologically safe in animals, and further purification is not needed.

Example 5

This example provides a method for washing and regenerating microfiltration membrane and ultrafiltration membrane. The specific steps are as follows:

(1) Pure water was separately added to the microfiltration device and ultrafiltration device in the integrated filtration system with two membranes in combination after use in Examples 1-3, to wash microfiltration membrane and ultrafiltration membrane therein, respectively. During the wash process, the shear rate through membrane was increased to 16000 s$^{-1}$, and the transmembrane flux was increased from 10 LMH to 50 LMH gradually.

(2) After washing in Step (1), 0.1-0.5 M NaOH solution was separately added to the microfiltration device and the ultrafiltration device for further washing. During this process, the solution temperature was 50° C., the shear rate was 16000 s$^{-1}$, the transmembrane flux was gradually increased from 50 LMH to 400 LMH, and the wash time was 60 min.

(3) After washing in Step (2), the microfiltration device and the ultrafiltration device were flushed with pure water using a wash and filtration mode until the pH of microfiltration filtrate and ultrafiltration filtrate was below 9.

(4) The shear flow rate was reduced to 2000 s$^{-1}$, the temperature was controlled at 20° C., the transmembrane flux was gradually increased from 5 LMH to 100 LMH, and the water flux of the system was determined and recorded.

Figure 5:
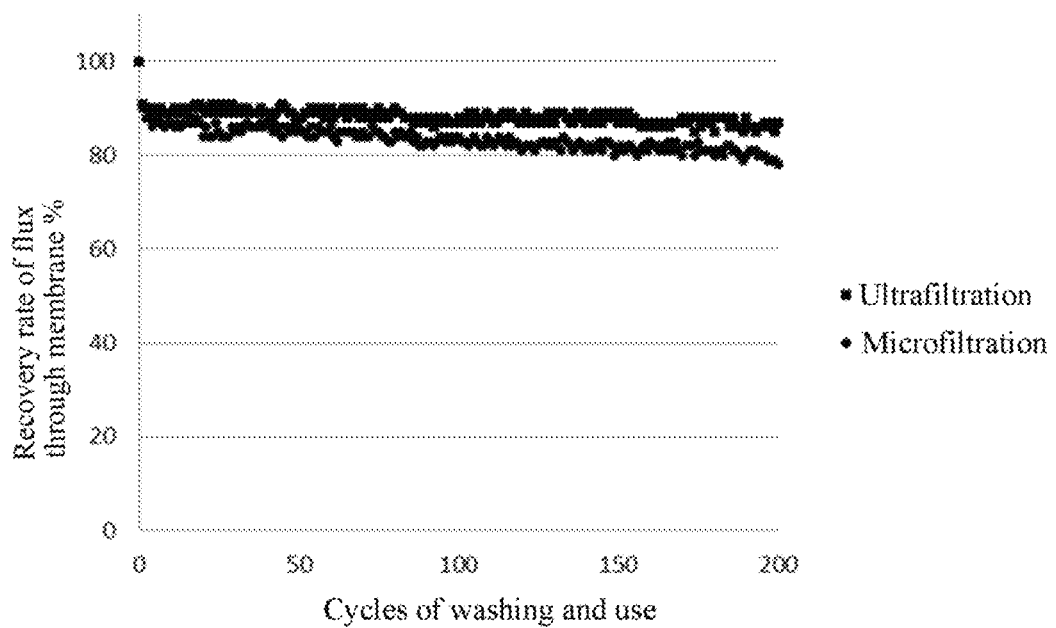
FIG. 5 shows the recovered value of water flux after 200 cycles of using the microfiltration membrane and the ultrafiltration membrane in Example 5 of the present application.

(5) The water flux through the microfiltration membrane and the ultrafiltration membrane was detected and recorded in 200 consecutive cycles of use, as shown in FIG. 5.

FIG. 5 shows that, during the 200 cycles of use, both the microfiltration membrane and the ultrafiltration membrane retained a good recoverability and consistency. Since both the microfiltration and ultrafiltration were carried out within the reversible contamination area greatly reducing of the membrane, the degree of membrane contamination and efforts to recover membrane were reduced. Furthermore, the recoverability of membrane was improved by multistage emission of contaminants and hot-water wash before using detergents. According to the data of water flux through membrane, the membrane was in a stable state during 200 cycles of use, which is 5-10 times more than the membrane's service life in a conventional process. Therefore, equipment and consumables input was greated reduced, and the production cost was reduced as well.

In summary, under some optimized experimental conditions, a linear scale-up process was achieved by using an integrated filtration system with two membranes in combination adopted in the present invention. The scale-up process inherited some advantages from laboratory-scale process, including a high recovery and a high impurities removal rate. In a scaled-up production process, the volume of two feed tanks (namely, the microfiltration feed tank and the concentration tank) in the integrated filtration system with two membranes in combination is close to that of the liquid concentrated, and is 10-20 times smaller than the volume of two conventionally used feed tanks, which have an equal volume to the pretreated feed tank. Thus, the process time is shortened by half. Most importantly, the present vaccine preparation method using an integrated filtration system with two membranes in combination achieved the same high recovery and purity as that by multistep procedures, which is commonly used in a traditional FMD vaccine preparation process.

Specific embodiments of the present invention are described above. It should be understood that the present invention is not limited to the above specific embodiments, and various variations or modifications can be made by those skilled in the art without departing from the scope of the claims, which do not affect the essence of the present invention. The embodiments and the features in the embodiments may be combined with each other without conflict.

What is claimed is:

1. A method for preparing a foot and mouth disease (FMD) vaccine, comprising the following steps:
   (i) obtaining cell culture media containing FMD virus;
   (ii) separating and purifying the cell culture media containing FMD virus by passing through an integrated filtration system with two membranes in combination, which comprises a microfiltration device and an ultrafiltration device arranged in parallel, wherein the microfiltration device comprises a microfiltration feed tank, a first main pump, and a microfiltration membrane, and the ultrafiltration device comprises a concentrate tank, a second main pump, and an ultrafiltration membrane; wherein the microfiltration device is configured to remove large-particle impurities in the cell culture media containing FMD virus, and the ultrafiltration device is configured to remove small molecular impurities in the cell culture media containing FMD virus; wherein the microfiltration device and the ultrafiltration device run simultaneously to perform microfiltration and ultrafiltration of the cell culture media containing FMD virus at the same time to thereby form a concentrate containing FMD virus in the concentrate tank; wherein the microfiltration device is connected to a first constant flow pump, and the ultrafiltration device is connected to a second constant flow pump so as to dynamically control the transmembrane flux, the transmembrane flux is 65-100% of the critical membrane flux of the microfiltration membrane or the ultrafiltration membrane, the volume of the concentrate tank is 1/5-1/50 of the initial volume of the cell culture media containing FMD virus, and the volume of the concentrate tank is equal to or not more than 1.5 times of the target concentrate volume of the cell culture media containing FMD virus;
   (iii) collecting the concentrate containing FMD virus obtained in step (ii).

2. The method according to claim 1, wherein after at least a portion of the cell culture media containing FMD virus passing through the microfiltration device, a first diafiltration buffer is further added to the microfiltration feed tank and allowed to pass through the integrated filtration system with two membranes in combination, to obtain a concentrate.

3. The method according to claim 2, wherein the volume of the first diafiltration buffer added is 1-5 times of the volume of the microfiltration retentate.

4. The method according to claim 1, wherein the ultrafiltration filtrate obtained in step (ii) is added as a first diafiltration buffer to the microfiltration feed tank, and allowed to pass through the integrated filtration system with two membranes in combination, to obtain a concentrate.

5. The method according to claim 1, wherein a second diafiltration buffer is added to the concentrate containing FMD virus obtained in step (ii) to allow small molecular impurities in the concentrate to pass through the ultrafiltration membrane, and thereby to obtain a purified viral concentrate.

6. The method according to claim 5, wherein the volume of the second diafiltration buffer added is 1-10 times of the volume of the viral concentrate.

7. The method according to claim 1, wherein the first constant flow pump is disposed at the penetration end of the microfiltration device, and the second constant flow pump is disposed at the penetration end of the ultrafiltration device.

8. The method according to claim 1, wherein the transmembrane flux is 10-150 LMH.

9. The method according to claim 1, wherein the shear rate through the microfiltration membrane and the ultrafiltration membrane is 1500-4000 $s^{-1}$.

10. The method according to claim 1, wherein a material per unit membrane area of the microfiltration membrane and the ultrafiltration membrane is 10-500 L/m2.

11. The method according to claim 1, wherein the microfiltration device and the ultrafiltration device are regenerated by washing after step (iii).

12. The method according to claim 11, wherein the regeneration by washing comprises the following steps:
   a) add pure water to the microfiltration device and the ultrafiltration device to wash the microfiltration membrane and the ultrafiltration membrane separately, during the washing process, increasing the shear rate through membrane to 8000-16000 $s^{-1}$, and controlling the transmembrane flux at 10-500 LMH;
   b) after the washing process in step a), adding 0.1-0.5 M NaOH solution to further wash the microfiltration device and the ultrafiltration device, controlling the temperature of the solution at 45-55° C., the shear rate through membrane at 8000-16000 $s^{-1}$, the transmembrane flux at 50-500 LMH, and the time at 30-60 min;
   c) after the washing process in step (b), flushing the microfiltration device and the ultrafiltration device with pure water separately until the pH value of the microfiltration filtrate and the ultrafiltration filtrate is declined to 9 or less.

13. An apparatus for preparing an FMD vaccine, comprising an integrated filtration system with two membranes in combination, wherein the integrated filtration system with two membranes in combination comprises a microfiltration device and an ultrafiltration device arranged in parallel, wherein the microfiltration device comprises a microfiltration feed tank, a first main pump, and a microfiltration membrane; and the ultrafiltration device comprises a concentrate tank, a second main pump, and an ultrafiltration membrane, wherein the microfiltration device is configured to remove large-particle impurities in the cell culture media containing FMD virus, and the ultrafiltration device is configured to remove small molecular impurities in the cell culture media containing FMD virus, wherein the microfiltration device and the ultrafiltration device run simultaneously to perform microfiltration and ultrafiltration of the cell culture media containing FMD virus at the same time to thereby form a concentrate containing FMD virus in the concentrate tank, wherein the integrated filtration system with two membranes in combination comprises a first constant flow pump and a second constant flow pump, wherein the microfiltration device is connected to the first constant flow pump, and the ultrafiltration device is connected to the second constant flow pump so as to dynamically control the transmembrane flux.

14. The apparatus according to claim 13, wherein the microfiltration device and the ultrafiltration device are connected to each other, such that both the microfiltration filtrate and the ultrafiltration retentate are retained in the concentrate tank to form a concentrate containing FMD virus.

15. The apparatus according to claim 13, wherein the first constant flow pump is disposed at the penetration end of the microfiltration device, and the second constant flow pump is disposed at the penetration end of the ultrafiltration device.

* * * * *